United States Patent [19]

Abdo

[11] Patent Number: 5,671,497
[45] Date of Patent: Sep. 30, 1997

[54] APPLICATOR FOR APPLYING LOTION TO HARD-TO-REACH AREAS OF BODY

[76] Inventor: Joel M. Abdo, 11830 208th Pl. SE., Issaquah, Wash. 98027

[21] Appl. No.: 599,027

[22] Filed: Feb. 9, 1996

Related U.S. Application Data

[63] Continuation-in-part of Ser. No. 494,067, Jun. 23, 1995, abandoned.

[51] Int. Cl.$^6$ .................... B25G 1/02; A47K 7/02
[52] U.S. Cl. .................... 15/144.1; 15/244.1; 15/244.3
[58] Field of Search .................... 15/104.94, 144.1, 15/244.1, 244.3; 401/6

[56] References Cited

U.S. PATENT DOCUMENTS

| | | |
|---|---|---|
| 1,478,388 | 12/1923 | Gray . |
| 1,649,089 | 11/1927 | Volckening .................... 15/244.1 |
| 1,820,256 | 8/1931 | Stewart . |
| 2,877,483 | 3/1959 | Alvistur . |
| 2,929,087 | 3/1960 | Salmon .................... 15/244.1 |
| 2,942,285 | 6/1960 | Gray . |
| 3,131,409 | 5/1964 | Davis .................... 15/244.1 |
| 3,419,931 | 1/1969 | Willig .................... 15/144.1 |
| 3,568,237 | 3/1971 | Rhodes . |
| 3,849,225 | 11/1974 | Haertle . |
| 4,015,306 | 4/1977 | Fenster . |
| 4,381,766 | 5/1983 | Avolio . |
| 4,396,028 | 8/1983 | Waggoner .................... 15/144.1 |
| 4,475,836 | 10/1984 | Colognori . |
| 4,483,356 | 11/1984 | Kales . |
| 4,615,066 | 10/1986 | Colognori . |
| 4,934,011 | 6/1990 | Haug . |
| 5,003,659 | 4/1991 | Paepke . |
| 5,033,155 | 7/1991 | Klotz . |
| 5,158,532 | 10/1992 | Peng et al. . |
| 5,240,339 | 8/1993 | DeForest et al. . |
| 5,419,015 | 5/1995 | Garcia . |
| 5,437,372 | 8/1995 | Per-Lee . |

FOREIGN PATENT DOCUMENTS

| | | |
|---|---|---|
| 0 175 260 | 3/1986 | European Pat. Off. . |
| 1247167 | 10/1960 | France .................... 15/144.1 |
| 357843 | 12/1961 | Switzerland .................... 15/144.1 |

Primary Examiner—David Scherbel
Assistant Examiner—Randall Chin
Attorney, Agent, or Firm—Joan H. Pauly

[57] ABSTRACT

An applicator for applying substances, such as lotions, to a user's body has a handle, an attachment member, and a pad removably attached to the attachment member. The handle has a rigid portion with a gripping member at one end and an opposite end portion received into the axial opening of a sleeve. An end of a bendable section is removably received into the axial opening opposite the rigid portion. The attachment member includes a flat layer and a formed layer with edge portions secured to the flat layer. A midportion of the formed layer extends around and is secured to the end of the bendable section opposite the sleeve. The flat face of the attachment member preferably forms a hook component of a hook and loop fastener for easy attachment to a fabric face of a pad.

10 Claims, 4 Drawing Sheets

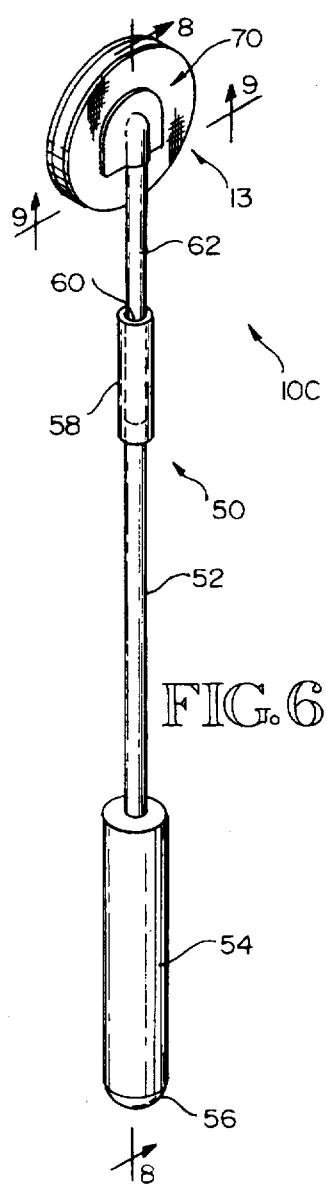
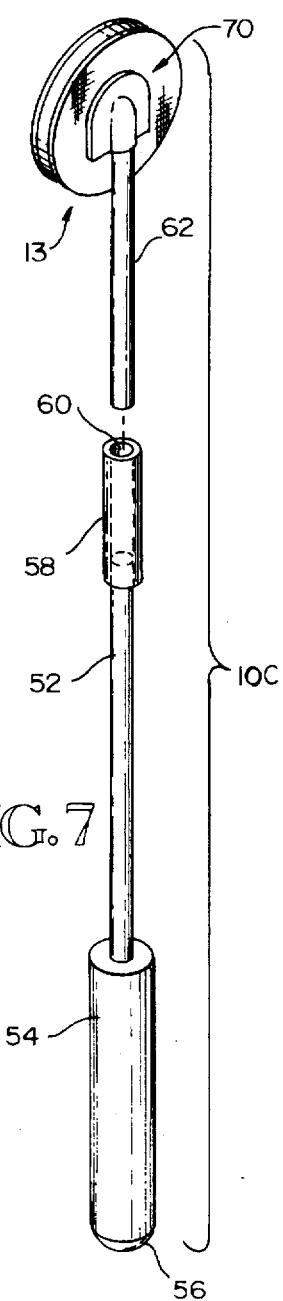
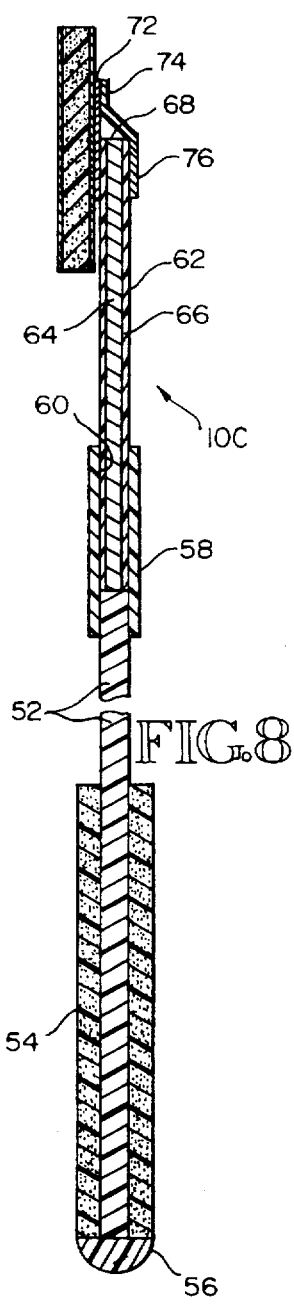
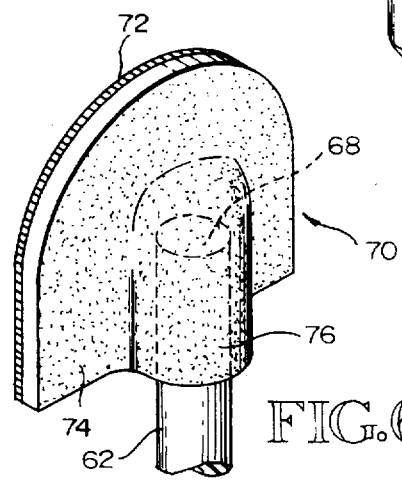
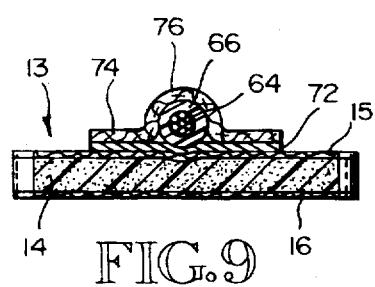

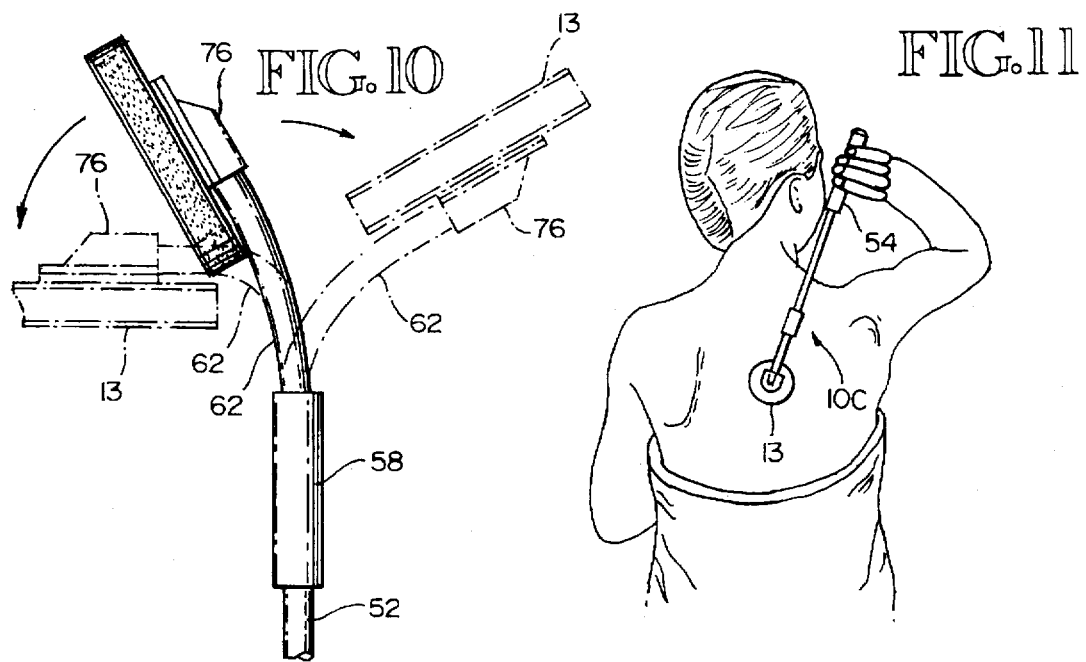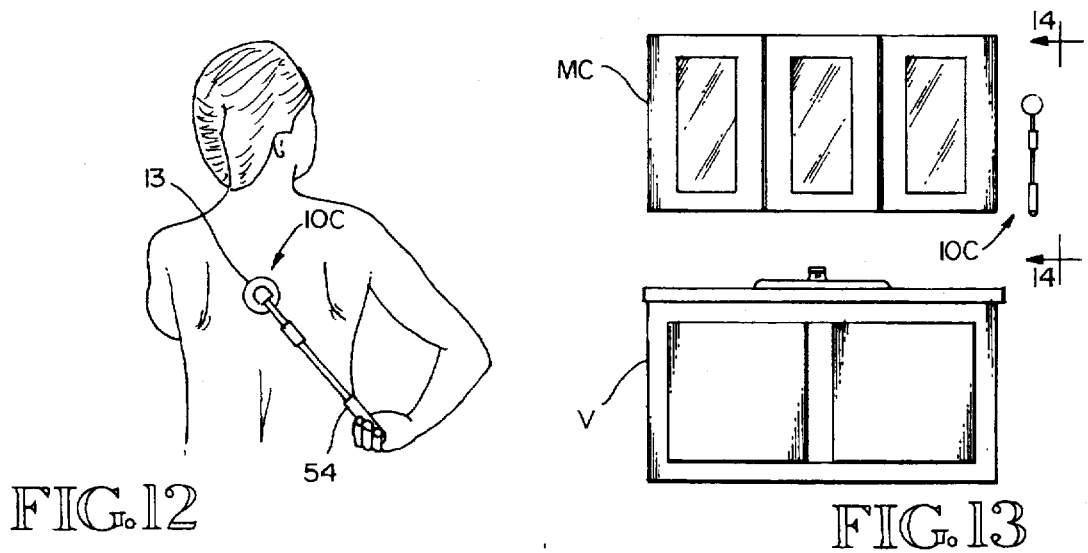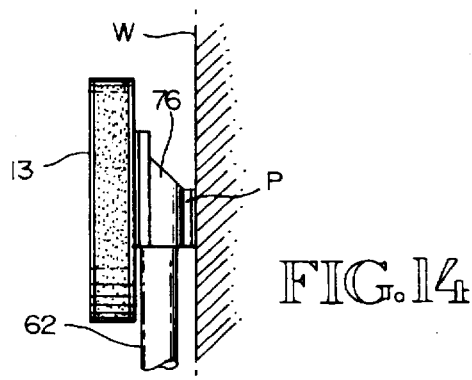

APPLICATOR FOR APPLYING LOTION TO HARD-TO-REACH AREAS OF BODY

RELATED APPLICATION

This application is a continuation-in-part of the applicant's U.S. patent application Ser. No. 08/494,067, filed Jun. 23, 1995, now abandoned.

TECHNICAL FIELD

The present invention relates to hand held implements for applying medications, such as medicated lotions, to the body of a user. More particularly, it relates to such implements that are adapted to self application, by a user, of lotions to various hard-to-reach areas of the user's body, such as the user's back.

BACKGROUND INFORMATION

The following patents were found in a search relating to the invention disclosed in the aforementioned U.S. patent application Ser. No. 08/494,067: U.S. Pat. No. 3,568,237, granted Mar. 9, 1971, to W. L. Rhodes; No. 4,475,836, granted Oct. 9, 1984, to A. Colognori; No. 4,615,066, granted Oct. 7, 1986, to A. Colognori; No. 4,934,011, granted Jun. 19, 1990, to Christopher B. Haug; and No. 5,240,339, granted Aug. 31, 1993, to DeForest et al. Each of the listed patents covers an implement adapted to washing or applying lotion to areas of a person's body that are difficult to reach.

Devices for applying skin treatment substances are also disclosed in U.S. Pat. No. 4,381,766, granted May 3, 1983, to A. M. Avolio; No. 4,483,356, granted Nov. 20, 1984, to D. R. Kales; and No. 5,437,372, granted Aug. 1, 1995, to M. S. Per-Lee. An applicator pad for automobile polish having a resilient foam core covered by layers of heat-sealable film and outer fabric is disclosed in U.S. Pat. No. 4,015,306, granted Apr. 5, 1977, to L. A. Fenster.

SUMMARY OF THE INVENTION

The subject of the invention is an applicator for applying substances to hard-to-reach portions of a user's body. The applicator comprises a handle having a first end configured to be gripped by a user and a second opposite end, an attachment portion carried by the second end, and a pad removably attachable to the attachment portion. According to an aspect of the invention, the handle includes a rigid portion, a sleeve, and a bendable portion. The rigid portion extends from the first end to an opposite end portion. The sleeve has an axial opening into which this opposite end portion is received. The bendable portion has opposite end portions received into the axial opening and engaging the attachment portion, respectively. At least one of the rigid and bendable portions is removably received into the axial opening to provide a detachable connection between the rigid portion and the bendable portion.

In the preferred embodiment, the pad comprises a foam core sandwiched between opposite outer layers of fabric and an interface between the core and each fabric layer. The layers are sufficiently absorbent to apply lotions to a body. Each interface is sufficiently impermeable to substantially prevent passage of a lotion through the interface into the core. Preferably, the attachment portion includes a hook component of a hook and loop fastener. The hook component is removably attachable to either of the fabric layers by pressing the component and the layer together.

A preferred feature of the attachment portion is opposite faces each of which comprises a component of a hook and loop fastener. The pad is removably attachable to one of the faces by pressing the pad and the face together. The other of the faces is removably attachable to a separate component of a hook and loop fastener carried by a structure for storing the applicator.

The bendable portion of the handle may be formed in various ways. Preferably, the bendable portion comprises a bendable metal core and a cylindrical outer plastic covering. Whatever the details of the structure of the bendable portion, the bendable portion may comprise a plurality of bendable sections to achieve a greater degree of bending. A sleeve releasably connects adjacent ends of each adjacent pair of bendable sections.

According to another aspect of the invention, the attachment portion comprises an attachment member carried by the second end. The attachment member comprises a substantially flat portion having an inwardly directed face and an opposite outwardly directed face. The outwardly directed face forms a hook component of a hook and loop fastener. The attachment member also includes a formed portion having substantially flat edge portions secured to the inwardly directed face of the flat portion and a midportion extending around and attached to the second end of the handle. The pad is removably attachable to the outwardly directed face by pressing the outwardly directed face and the pad together.

A preferred feature is adhesive attachment of the flat portion and the formed portion to the second end of the handle. Another preferred feature is a formed portion that comprises an outwardly directed loop component of a hook and loop fastener for removably attaching the attachment member, and thereby attaching the applicator, to a separate hook component carried by a structure for storing the applicator. The handle configuration with a bendable portion is preferably provided in combination with an attachment member that has flat and formed portions.

The invention has a number of advantages. These advantages, the features of the invention discussed above, and further features will become apparent from the detailed description of the best modes for carrying out the invention that follows.

BRIEF DESCRIPTION OF THE DRAWINGS

In the drawings, like element designations refer to like parts throughout, and:

FIG. 6 is a pictorial view of the currently most preferred embodiment of the invention.

FIG. 6A is a fragmentary pictorial view of the attachment member and a portion of the handle shown in FIG. 6.

FIG. 7 is like FIG. 6 but shows the handle portions detached from each other.

FIG. 8 is a sectional view taken along the line 8—8 in FIG. 6.

FIG. 9 is a cross-sectional view taken along the line 9—9 in FIG. 6.

FIG. 10 is a side elevational view of an end portion of the applicator shown in FIG. 6 including the bendable handle portion, illustrating in phantom positions into which the bendable portion may be bent.

FIG. 11 is a pictorial view illustrating use of the applicator shown in FIG. 6 by reaching over the shoulder.

FIG. 12 is like FIG. 11 except that it shows use of the applicator by reaching around the waist toward the back.

FIG. 13 is an elevational view of a typical vanity arrangement in a residential bathroom and illustrates the storage of the applicator by hanging it on a wall.

FIG. 14 is a fragmentary side elevational view of the portion of the applicator that is secured to the wall in FIG. 13.

BEST MODES FOR CARRYING OUT THE INVENTION

Figure 1:
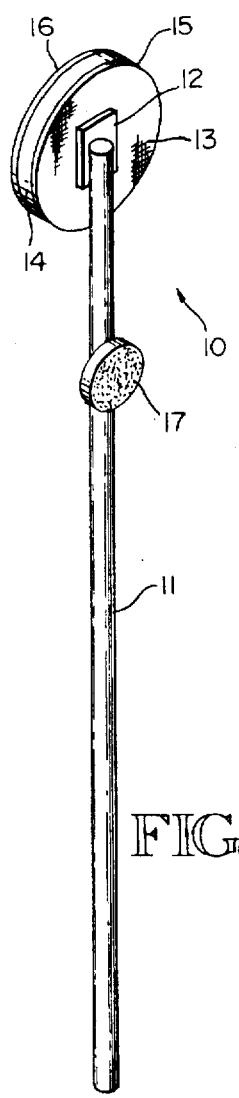
FIG. 1 is a pictorial view of a first embodiment of the invention.

The subject invention is an applicator for applying lotion or other substances to areas on a user's body hard to reach by the user of the applicator. FIG. 1 illustrates a first embodiment of the applicator. Applicator 10 comprises an elongated handle 11, a patch 12 of hook component material of a hook and loop fastening system, and applicator pad assembly 13. Patch 12 is adhesively attached to one end of the handle 11. The pad assembly 13 comprises a flat, cylindrical body 14 made of soft, open-cell foam and circular fabric layers 15 and 16 laminated to the circular surfaces of the body 14. The material of the fabric layers 15, 16 is marketed by the VELCRO™ Company and, while having smooth, even surfaces, functions as the loop component in a loop and hook fastening. The pad assembly is therefore detachably attachable to patch 12. Patch 17 adhesively attached to the handle is used in conjunction with a cooperating patch of VELCRO™ material attached to a wall or the like to hang the implement up for storage.

The applicator of the invention may include various types of pads. Currently, the type of pad shown in FIGS. 1–3 and 6–16 is preferred for inclusion in all of the embodiments of the invention. As noted above, the pad 13 comprises a foam core 14 sandwiched between opposite outer layers of fabric 15, 16. An interface is formed between the core 14 and each of the layers 15, 16. The layers are preferably made from a material, such as nylon, that is sufficiently absorbent to apply lotions to a body. The interfaces between the fabric layers 15, 16 and the foam core 14 are preferably sufficiently impermeable to substantially prevent passage of a lotion through the interface into the core 14. This desired impermeability may be achieved, for example, during manufacture of the pad by using heat and pressure to secure the fabric layers 15, 16 to the core 14. The use of heat causes a small degree of melting of the outer surface of the core 14 to allow the melted material to penetrate the fabric 15, 16 to interlock with the fabric 15, 16 and thereby secure the fabric 15, 16 to the core 14. The interlocking portions of the core 14, when cooled, have the desired impermeable characteristic. However, the fabric layers 15, 16 remain sufficiently soft and absorbent to apply lotion to the skin and to be rubbed against the skin without causing irritation. The fabric layers 15, 16 also retain their ability to function as loop components of a hook and loop fastener. As shown, the pad 13 has a circular configuration. It could also have various other configurations.

Figure 2:
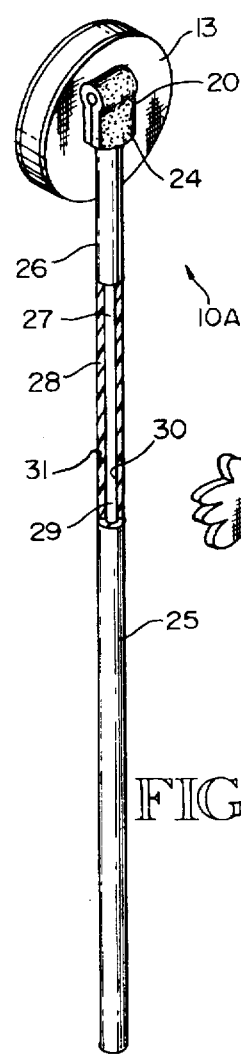
FIG. 2 is a pictorial view of a second embodiment of the invention having a bendable handle portion.

FIG. 2 shows a second embodiment of the subject invention. Applicator 10A comprises a handle assembly 25, 26, a pad assembly 13 as described above, and a hook component patch 20 of VELCRO™ material folded over one end of the handle assembly with adjoining portions of the edges of the patch 20 joined to form the patch 20 into a glove. The glove is held in place on the handle end by an adhesive. Pad assembly 13 is detachably attached to one face of the glove. The opposite face 24 can be used in cooperation with a VELCRO™ patch fastened on a wall or the like to hang up the applicator for storage. The handle assembly comprises a rigid portion 25 and a manually bendable portion 26 which allows for adjustment of the pad orientation relative to the handle. The bendable portion comprises a compliant metal rod or wire 27 encased in a plastic tube 28. End 29 of the wire 27 is adhesively attached in hole 30 in end 31 of the rigid portion 25 of the handle.

Figure 3:
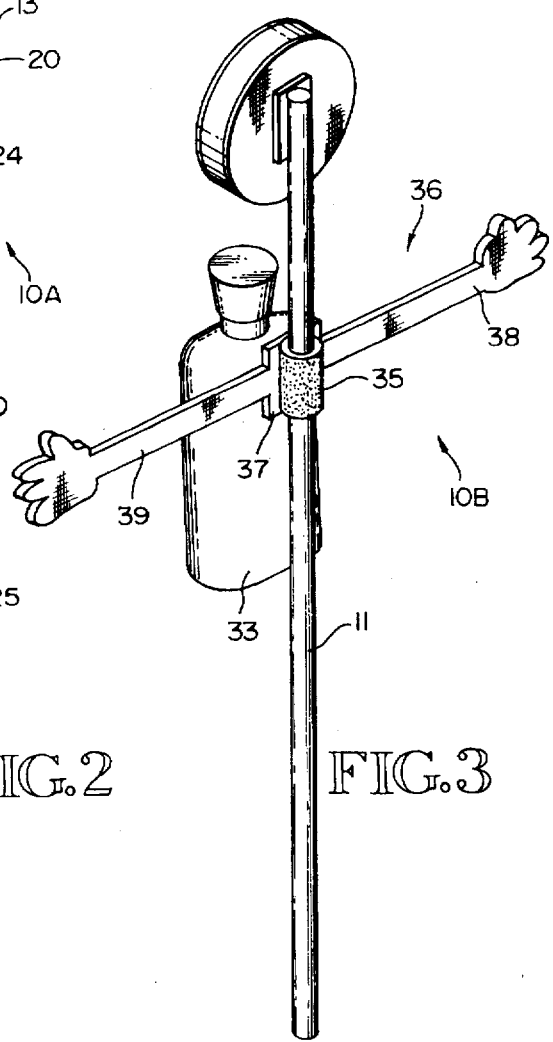
FIG. 3 is a pictorial view of a third embodiment, similar to that of FIG. 1 but further comprising means for attaching a container to the handle.

FIG. 3 illustrates a third embodiment of the invention. Applicator 10B comprises the applicator of FIG. 1 modified to include means for detachably attaching container 33 to handle 11. The means for attaching comprises a cylinder 35 of hook component VELCRO™ material surrounding the handle 11 and adhesively attached to it, and a loop component 36 having a center portion 37 and arm and hand-like portions 38 and 39 extending from the center portion perpendicular to the handle 11. The container is fitted with VELCRO™ patches to enable it to be attached to cylinder 35 and to enable fastening the arm and hand-like portions to the container to fasten it more securely to the handle. These patches are not visible in this view.

As shown in FIG. 3, the center portion 37 of the loop component 36 is positioned between the cylinder 35 and the container 33. An alternate arrangement, which may be preferable, is to position the center portion 37 and the container 33 on opposite sides of the cylinder 35. This can provide a more secure attachment of the container 33 to the applicator 10B. Another variation would be to provide one of the hand-like ends of the loop component 36 with a patch of hook component to enable the hands to be detachably secured together to grasp an ordinary container that does not itself carry any hook and loop fastener components.

Figure 4:
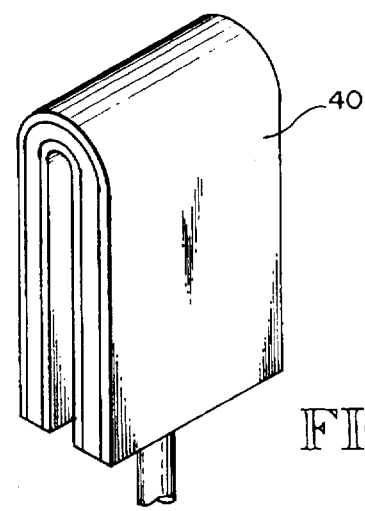
FIG. 4 is a pictorial view of the head portion of an applicator illustrating an alternate pad configuration.

In all of the embodiments, the handle may be telescopic to facilitate storage of the applicator in smaller volumes. Also, a grip may be installed on the end of the handle opposite the end to which the pad is attached. Further, in the embodiments comprising the glove at the tip of the handle, two pads may be installed. Also, on embodiments comprising the glove, an elongated pad may be used as shown in FIG. 4. Pad 40 is folded and attached to the glove, which is not visible in this view.

Figure 5:
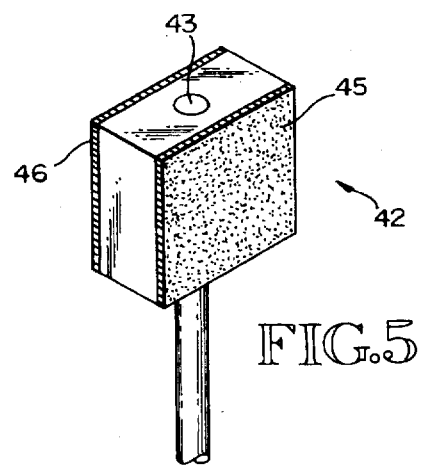
FIG. 5 is a pictorial view of the head portion of an applicator with the pad omitted to illustrate an adaptor mounted on an end of the handle to facilitate attachment of fastener hook components.

FIG. 5 illustrates an alternate embodiment of the head portion of the applicator in which an adaptor 42 is mounted on end 43 of the handle. The adaptor 42 facilitates adhesive attachment of fastener hook component patches 45 and 46. These patches may also be attached back to back to each other without the adaptor. Also one of the patches may be loop material, possibly the same material from which fabric layers 15 and 16 are made.

FIGS. 6–16 illustrate another embodiment of the applicator 10C which is currently the preferred embodiment. Referring to FIGS. 6, 7, and 8, the applicator 10C has a handle 50 that includes a rigid rod 52 and a bendable portion 62. An outer end portion of the rigid rod 52 is surrounded by a firm foam sleeve 54 that provides a means for easily and firmly gripping the end of the applicator 10C. The sleeve 54 is secured in position by a semispherical end piece 56. The end portion of the rod 52 opposite the cylindrical grip 54 is received into an axial opening 60 in a sleeve 58. As shown, the axial opening 60 extends all the way through the sleeve 58 without interruption. Alternatively, the axial opening could have a divider wall at a midportion thereof. The rod 52 and sleeve 58 are both preferably made from a strong, substantially rigid but non-brittle plastic.

The bendable portion of the handle 50 comprises a bendable section 62 having a circular cross section. As shown in FIGS. 8 and 9, the bendable section 62 includes a multi-strand metal core 64 encased in a cylindrical outer plastic covering 66. Both the metal core 64 and the plastic covering 66 are sufficiently flexible to allow the bendable section 62 to be easily bent in a curved configuration and back into the straight configuration shown in FIGS. 6, 7, and 8. The metal core 64 holds the bendable section 62 in a configuration into which it has been bent by a user until a user again applies force to change the degree of bending of the section 62. One end of the bendable section 62 is received into the axial opening 60 in the sleeve 58 through the end of the sleeve 58 opposite the rigid rod 52. FIG. 6 shows both the rigid rod 52 and the bendable section 62 with one end received into the axial opening 60 so that the sleeve 58 interconnects the two handle portions 52, 62.

Preferably, each of the handle members 52, 62 has a frictional fit in the axial opening 60 so that the members 52, 62 will remain in position relative to each other during use of the applicator 10C. Also preferably, one of the members 52, 62 has a frictional fit that is tight enough to maintain the member in position during use but loose enough to enable easy disengagement of the member 52, 62 from the sleeve 58. In the preferred embodiment, the bendable section 62 is more easily disengaged from the sleeve 58. This enables removal of the bendable section 62 and pad 13 carried thereby for cleaning or for replacement.

The outer end portion 68 of the bendable section 62 opposite the end that is received in the axial opening 60 in the sleeve 58 is attached to a pad 13 by means of an attachment member 70. The attachment member 70, best seen in FIG. 6A, includes a substantially flat portion 72 and a formed portion 74, 76. The substantially flat portion 72 has an inwardly directed face and an opposite outwardly directed face that forms a hook component of a hook and loop fastener. Either one of the fabric layers 15, 16 of a pad 13 may be releasably attached to the outwardly directed hook component face by pressing the hook component and the pad 13 together. This, in effect, attaches the pad 13 to the cylindrical side surface of the bendable section 62.

The formed portion 74, 76 has substantially flat edge portions 74 that are secured to the inwardly directed face of the flat portion 72, preferably by an adhesive. The formed portion 74, 76 also includes a midportion 76 partially surrounded by the flat edge portions 74. The midportion 76 is formed around and extends around and is attached to the outer end portion 68 of the bendable section 62 of the handle 50. As shown, the attachment member 70 has a dome configuration and the edge portions 74 of the formed portion 74, 76 extend around all but the straight end of the dome configuration opposite the curved end. This is the preferred configuration of the attachment member 70, but the attachment member may also have various other configurations. Both portions 72 and 74, 76 of the attachment member 70 are preferably adhesively attached to the handle's outer end portion 68.

In the preferred embodiment shown in FIGS. 6-16, the outer surface of the formed portion 74, 76 facing away from the flat portion 72 comprises an outwardly directed loop component of a hook and loop fastener. Generally, the loop component of such a fastener is more flexible than the hook component. Therefore, the preferred composition of the attachment member 70 takes advantage of the relative flexibility of the loop component to shape the attachment member 70 around the end 68 of the handle 50 while avoiding the problem of cracking of a hook component that can occur when a hook component is shaped into a curved configuration. In addition, the use of a formed portion 74, 76 with an outwardly directed loop component provides a means for removably attaching the attachment member 70, and thereby attaching the applicator 10C, to a separate hook component carried by a structure for storing the applicator 10C. Such an arrangement is illustrated in FIGS. 13 and 14. FIG. 13 shows a typical bathroom arrangement in which a vanity V is positioned below a medicine cabinet MC. A patch P (FIG. 14) of hook component is secured to the wall W adjacent to the medicine cabinet MC. The applicator 10C can be hung on the wall for drying and/or storage simply by pressing the outer surface of the attachment member formed portion 74, 76 against the patch P.

Figure 16:
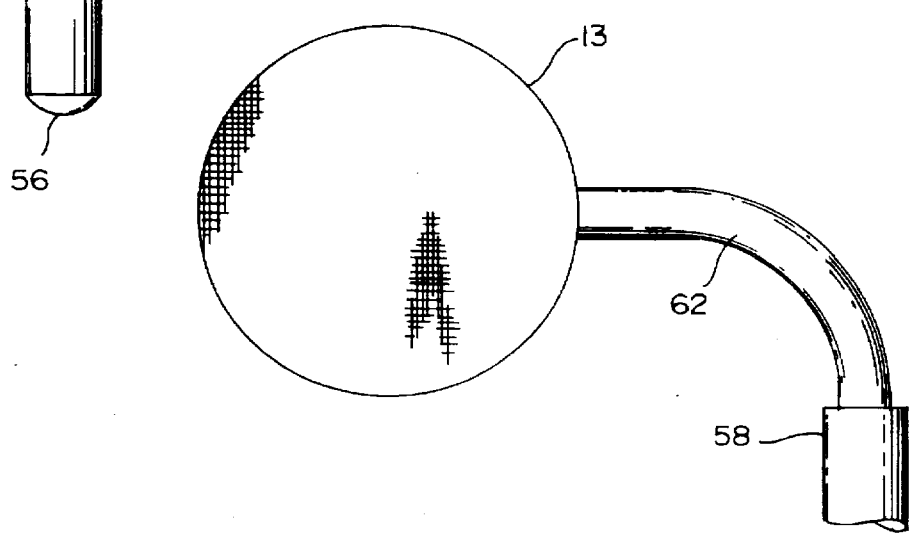
FIG. 16 is a fragmentary elevational view illustrating an additional orientation of the bendable portion of the handle and attached pad.

FIGS. 10 and 16 illustrate the bending of the bendable portion 62 of the handle 50 to adjust the position of the pad 13 relative to the handle grip 54. FIG. 10 illustrates adjustment of the bendable portion 62 by bending in either direction relative to the axis of the rigid portion 52 of the handle 5D about an axis parallel to the plane of the pad 13. FIG. 10 also illustrates three degrees of bending that may be achieved in either direction. FIG. 16 illustrates bending relative to the handle axis about a pivot axis perpendicular to the plane of the pad 13. A user may adjust the pad orientation by bending about either or both the parallel and perpendicular pivot axes until a pad orientation most comfortable to the individual user is achieved.

FIGS. 11 and 12 illustrate use of the applicator 10C. The illustrated uses include an over-the-shoulder use position, shown in FIG. 11, and an around-the-waist from front to back use position, shown in FIG. 12. The advantage of one use position over the other depends on the flexibility and movement limitations of the individual user, as well as individual preferences.

Figure 15:
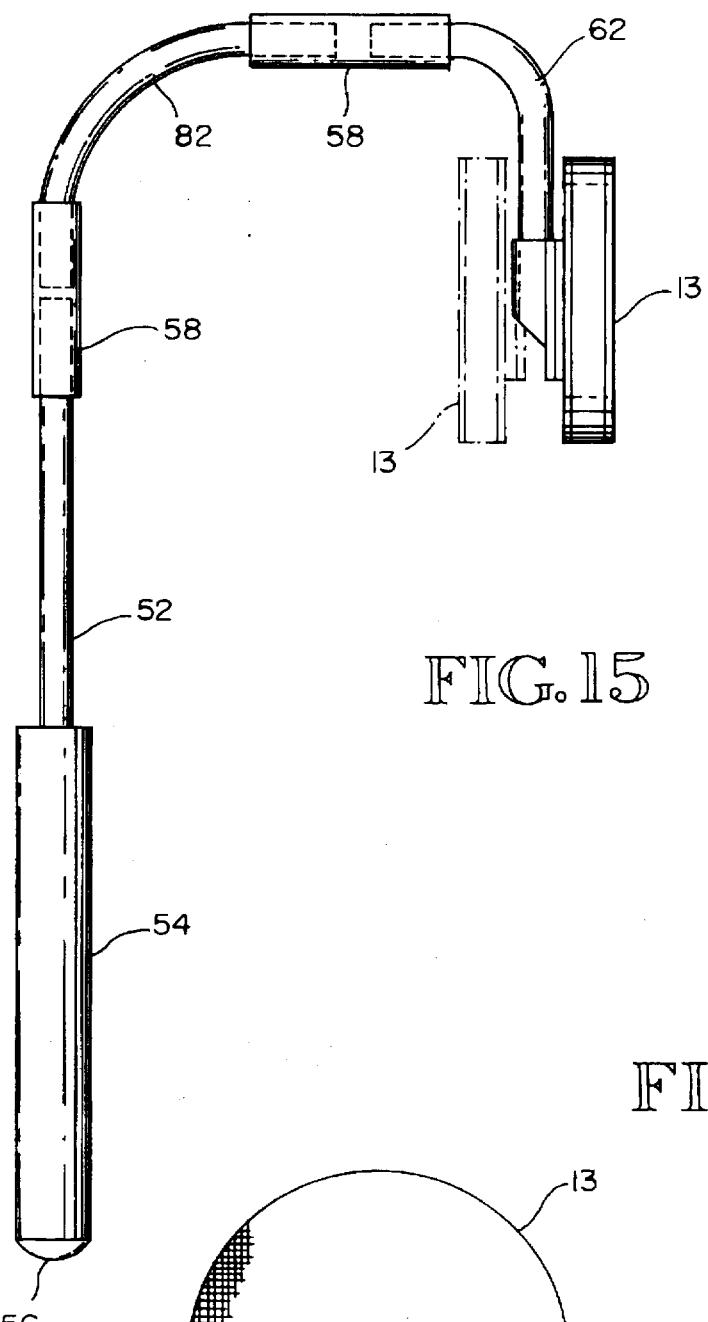
FIG. 15 is a side elevational view of a modification of the embodiment shown in FIG. 6 in which an additional bendable section is added to the handle.

FIG. 15 illustrates a modification of the applicator 10C. In the modification, the handle is provided with an additional bendable section 82 and two sleeves 58. As in FIG. 6, the first bendable section 62 has one end attached to the attachment member 70 and an opposite end received into one of the sleeves 58. The additional bendable section 82 is positioned between the rigid portion 52 and the first bendable portion 62. It has opposite ends received into the axial openings of the sleeve 58 which receives the first bendable portion 62 and another sleeve 58 which receives the end of the rigid portion 52. If desired, still further additional bendable sections could be provided. Preferably, all the sections have the same metal core/plastic covering structure. As illustrated in FIG. 15, the provision of an additional bendable section 82 increases the versatility of the pad orientation and the pad's position relative to the rigid and grip portions 52, 54 of the handle. The extended bendable portion 62, 82 of the handle may be bent around 180° to orient the pad 13 parallel to the rigid portion 52 but spaced therefrom. As shown in solid and phantom lines in FIG. 15, the pad may be oriented either facing away from or toward the rigid handle portion 52.

The applicator of the invention, and particularly the preferred embodiment thereof, has a number of advantages.

The applicator is easy and economical to manufacture. It is also very durable and highly versatile in its use. Although the bendable portion may be removed for cleaning or replacement, there are no small pieces that could be lost when the applicator is disassembled. The preferred characteristics of the pad allow lotion to be efficiently and easily applied to the body while maintaining easy cleaning of the pad and minimizing waste of the lotion. The pad may also be used for applying other types of substances, such as powdered substances. For a user, the applicator is easy to assemble, use, and maintain.

Although the preferred embodiments of the invention have been illustrated and described herein, it is intended to be understood by those skilled in the art that various modifications and omissions in form and detail may be made without departing from the spirit and scope of the invention as defined by the following claims.

What is claimed is:

1. An applicator for applying substances to hard-to-reach portions of a user's body, comprising:

a handle having a first end configured to be gripped by a user, and a second opposite end;

an attachment portion carried by said second end; and a pad removably attachable to said attachment portion;

wherein said handle includes a rigid portion extending from said first end to an opposite end portion, a sleeve having an axial opening into which said opposite end portion is received, and a bendable portion having opposite end portions received into said axial opening and engaging said attachment portion, respectively, at least one of said rigid portion and said bendable portion being removably received into said axial opening to provide a detachable connection between said rigid portion and said bendable portion; and wherein said bendable portion comprises a bendable metal core end a cylindrical outer plastic covering.

2. The applicator of claim 1, in which said bendable portion comprises a plurality of bendable sections, and a sleeve releasably connecting adjacent ends of each adjacent pair of bendable sections.

3. An applicator for applying substances to hard-to-reach portions of a user's body, comprising:

a handle having a first end configured to be gripped by a user, and a second opposite end;

an attachment member carried by said second end; said attachment member comprising a substantially flat portion having an outwardly directed face that includes a hook component of a hook and loop fastener; and a formed portion having a midportion extending around and attached to said second end; and a pad removably attachable to said outwardly directed face by pressing said outwardly directed face and said pad together;

in which said flat portion and said formed portion are adhesively attached to said second end.

4. The applicator of claim 3, in which said formed portion comprises an outwardly directed loop component of a hook and loop fastener for removably attaching said attachment member, and thereby attaching said applicator, to a separate hook component carried by a structure for storing said applicator.

5. The applicator of claim 3, in which said pad comprises a foam core sandwiched between opposite outer layers of fabric, and an interface between said core and each said layer; said layers being sufficiently absorbent to apply lotions to a body, and each said interface being sufficiently impermeable to substantially prevent passage of a lotion through said interface into said core; and said hook component of said attachment member being removably attachable to either of said layers by pressing said component and said layer together.

6. The applicator of claim 5, in which said attachment member further comprises a face opposite said hook component removably attachable to a separate hook component carried by a structure for storing the applicator.

7. An applicator for applying substances to hard-to-reach portions of a user's body, comprising:

a handle having a first end configured to be gripped by a user, and a second opposite end;

an attachment member carried by said second end; said attachment member comprising a substantially flat portion having an outwardly directed face that includes a hook component of a hook and loop fastener; and a formed portion having a midportion extending around and attached to said second end; and a pad removably attachable to said outwardly directed face by pressing said outwardly directed face and said pad together;

in which said formed portion comprises an outwardly directed loop component of a hook and loop fastener for removably attaching said attachment member, and thereby attaching said applicator, to a separate hook component carried by a structure for storing said applicator.

8. An applicator for applying substances to hard-to-reach portions of a user's body, comprising:

a handle having a first end configured to be gripped by a user, and a second opposite end;

an attachment portion carried by said second end; and a pad removably attachable to said attachment portion;

wherein said handle includes a rigid portion extending from said first end to an opposite end portion, and a bendable portion having opposite end portions extending from said opposite end portion of said rigid portion and engaging said attachment portion, respectively; and wherein said pad comprises a foam core sandwiched between opposite outer layers of fabric, and an interface between said core and each said layer; said layers being sufficiently absorbent to apply lotions to a body, and each said interface being sufficiently impermeable to substantially prevent passage of a lotion through said interface into said core; and said attachment portion includes a hook component of a hook and loop fastener, said component being removably attachable to either of said layers by pressing said component and said layer together.

9. The applicator of claim 8, in which said attachment portion includes opposite faces, each of which comprises a component of a hook and loop fastener, said pad is removably attachable to one of said faces by pressing said pad and said face together, and the other of said faces is removably attachable to a separate component of a hook and loop fastener carried by a structure for storing the applicator.

10. The applicator of claim 8, in which said bendable portion comprises a bendable metal core and a cylindrical outer plastic covering.

* * * * *

UNITED STATES PATENT AND TRADEMARK OFFICE
CERTIFICATE OF CORRECTION

PATENT NO: 5,671,497

DATED: September 30, 1997

INVENTOR(S): Joel M. Abdo

It is certified that error appears in the above-identified patent and that said Letters Patent is hereby corrected as shown below:

Claim 1, column 7, line 20, the semicolon should be a colon.

Claim 1, column 7, line 37, "end" should be -- and --.

Signed and Sealed this

Seventeenth Day of February, 1998

Attest:

BRUCE LEHMAN

Attesting Officer        Commissioner of Patents and Trademarks